(12) United States Patent
Niimoto et al.

(10) Patent No.: US 7,943,785 B2
(45) Date of Patent: May 17, 2011

(54) PROCESS FOR PRODUCING (Z)-1-PHENYL-1-(N,N-DIETHYLAMINOCARBONYL)-2-PHTHALIMIDOMETHYLCYCLOPROPANE

(75) Inventors: Yoshihide Niimoto, Kobe (JP); Hiroharu Kumazawa, Osaka (JP); Koh Kawami, Okayama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 781 days.

(21) Appl. No.: 11/795,860

(22) PCT Filed: Jan. 26, 2007

(86) PCT No.: PCT/JP2006/301711
§ 371 (c)(1),
(2), (4) Date: Jul. 24, 2007

(87) PCT Pub. No.: WO2006/080555
PCT Pub. Date: Aug. 3, 2006

(65) Prior Publication Data
US 2009/0292127 A1 Nov. 26, 2009

(30) Foreign Application Priority Data

Jan. 28, 2005 (JP) .................................. 2005-022188
May 18, 2005 (JP) .................................. 2005-145875

(51) Int. Cl.
*C07C 233/58* (2006.01)
*C07D 209/48* (2006.01)

(52) U.S. Cl. ........................................ 548/477; 564/163
(58) Field of Classification Search ................... 548/477
See application file for complete search history.

(56) References Cited

U.S. PATENT DOCUMENTS
5,034,541 A 7/1991 Bigg et al.

FOREIGN PATENT DOCUMENTS
EP 0 200 638 A1 4/1986
EP 1 770 084 A1 4/2007

OTHER PUBLICATIONS

R. Guilet et al., "Improvements in procedures of a bicyclic lactone synthesis: 1-phenyl-2-oxo-3-oxa-bicyclo [3:1:0] hexane", C.R. Avad. Sci. Paris, t. 1, Serie. II No. 2 ,1998, pp. 651-660.
B. Bonnaud, et al., "1-Aryl-2-(aminomethyl)cyclopropaner-carboxylic Acid Derivatives. A new Series of Potential Antidepressants", J. Med. Chem. 1987, vol. 30, No. 2, pp. 318-325.
B. Bonnaud, et al., "A Convenient Synthesis of Bifunctional Vicinal Cyclpropanes", Synthesis, 1978, pp. 304-305.

*Primary Examiner* — Shawquia Young
(74) *Attorney, Agent, or Firm* — Foley & Lardner LLP

(57) ABSTRACT

The present invention provides a process for producing (Z)-1-phenyl-1-(N,N-diethylaminocarbonyl)-2-phthalimido methylcyclopropane, which includes reacting (Z)-1-phenyl-1-(N,N-diethylamino-carbonyl)-2-hydroxymethylcyclopropane with an orthoester and a brønsted acid, and reacting the reaction product with a phthalimidating agent; and a process for producing (Z)-1-phenyl-1-(N,N-diethylaminocarbonyl)-2-aminomethylcyclopropane hydrochloride through the above process.

8 Claims, No Drawings

PROCESS FOR PRODUCING (Z)-1-PHENYL-1-(N,N-DIETHYLAMINOCARBONYL)-2-PHTHALIMIDOMETHYLCYCLOPROPANE

TECHNICAL FIELD

The present invention relates to a novel process for producing
(Z)-1-phenyl-1-(N,N-diethylaminocarbonyl)-2-aminomethylcyclopropane hydrochloride, which is useful as an antidepresent, and
(Z)-1-phenyl-1-(N,N-diethylaminocarbonyl)-2-phthalimidomethylcyclopropane as an intermediate thereof.

BACKGROUND ART (Z)-1-phenyl-1-(N,N-diethylaminocarbonyl)-2-phthalimidomethylcyclopropane (hereafter, may be referred to as the (Z)-phthalimidomethylcyclopropane compound) is an intermediate of a (Z)-1-phenyl-1-(N,N-diethylaminocarbonyl)-2-aminomethylcyclopropane hydrochloride (hereafter, (Z)-1-phenyl-1-(N,N-diethylaminocarbonyl)-2-aminomethylcyclopropane may be sometimes referred to as the (Z)-aminomethylcyclopropane compound, and (Z)-1-phenyl-1-(N,N-diethylaminocarbonyl)-2-aminomethylcyclopropane hydrochloride may be sometimes referred to as the (Z)-aminomethylcyclopropane compound hydrochloride, respectively), which is useful as an antidepresent. Conventionally, there has been known a process for producing the (Z)-phthalimidomethylcyclopropane compound, which comprises chlorinating (Z)-1-phenyl-1-(N,N-diethylaminocarbonyl)-2-hydroxymethylcyclopropane (hereafter, may be referred to as the (Z)-hydroxymethylcyclopropane compound) with thionyl chloride to obtain (Z)-1-phenyl-1-(N,N-diethylaminocarbonyl)-2-chloromethylcyclopropane, and reacting the product with a phthalimide salt (see, JP2964041-B).

DISCLOSURE OF THE INVENTION

An object of the present invention is to provide a process for producing the (Z)-phthalimidomethylcyclopropane compound and further the (Z)-aminomethylcyclopropane compound hydrochloride at high yield by a simple operation without using a reagent which may generate sulfur dioxide, such as, thionyl chloride, and a low boiling point halogenated hydrocarbon solvent.

The object and other objects of the present invention will become apparent from the following descriptions.

That is, the present invention is as follows.
<1> A process for producing (Z)-1-phenyl-1-(N,N-diethylaminocarbonyl)-2-phthalimidomethylcyclopropane which comprises reacting (Z)-1-phenyl-1-(N,N-diethylaminocarbonyl)-2-hydroxymethylcyclopropane with an orthoester and a brønsted acid, and then reacting the reaction product with a phthalimidating agent.
<2> The process according to <1>, wherein the reaction product of (Z)-1-phenyl-1-(N,N-diethylaminocarbonyl)-2-hydroxymethylcyclopropane, an orthoester and a brønsted acid is an iminium salt of the formula (I)

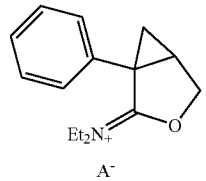

(I)

wherein A⁻ represents conjugated base of a brønsted acid.
<3> The process according to <1> or <2>, wherein the brønsted acid is methanesulfonic acid.
<4> The process according to any of <1> to <3>, wherein the orthoester is an orthoformic alkyl ester.
<5> The process according to <4>, wherein the orthoformic alkyl ester is triethyl orthoformate or trimethyl orthoformate.
<6> The process according to any of <1> to <5>, wherein the phthalimidating agent is (1) a phthalimide potassium salt or (2) phthalimide and a base.
<7> The process according to <6>, wherein the base is at least one selected from the group consisting of potassium tert-butoxide, sodium methoxide, potassium carbonate and triethylamine.
<8> The process according to any of <1> to <7>, wherein (Z)-hydroxymethylcyclopropane compound is the compound obtained by reacting 2-oxo-1-phenyl-3-oxabicyclo[3.1.0]hexane with diethylamine in the presence of an alkali metal alkoxide.
<9> A process for producing (Z)-aminomethylcyclopropane compound hydrochloride which comprises a step reacting (Z)-hydroxymethylcyclopropane compound with an orthoester and a brønsted acid to obtain reaction product,
a step reacting the reaction product with phthalimidating agent to obtain (Z)-phthalimidomethylcyclopropane compound,
a step reacting (Z)-phthalimidomethylcyclopropane compound with aqueous methylamine to obtain (Z)-aminomethylcyclopropane compound, and
a step treating (Z)-aminomethylcyclopropane compound with hydrogen chloride.
<10> An iminium salt of the formula (I)

(I)

wherein A⁻ represents conjugated base of a brønsted acid.
<11> The iminium salt according to claim 10, wherein A⁻ is CH₃SO₃⁻.

MODE FOR CARRYING OUT THE INVENTION

Hereinafter, the present invention will be described in detail.

The process for producing the (Z)-phthalimidomethylcyclopropane compound of the present invention includes the first step wherein the (Z)-hydroxymethylcyclopropane compound is reacted with an orthoester and a brønsted acid to produce an iminium salt (hereafter, may be referred to as the iminium salt (I)) of the formula (I):

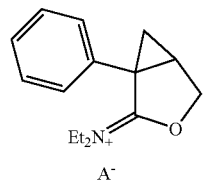

wherein A⁻ represents conjugated base of a brønsted acid, and the second step wherein the iminium salt (I) is reacted with a phthalimidating agent.

The first step can be conducted, for example, by mixing the (Z)-hydroxymethylcyclopropane compound, an orthoester and a brønsted acid in a solvent. Although an addition order is not particularly limited, a method of adding an orthoester to the (Z)-hydroxymethylcyclopropane compound and then adding a brønsted acid is preferable.

The orthoester is not particularly limited and easily available ones can be used. Examples thereof include orthoformicacid alkyl esters (such as trimethyl orthoformate and triethyl orthoformate), orthoaceticacid alkyl esters (such as trimethyl orthoacetate and triethyl orthoacetate), orthobutyricacid alkyl esters (such as trimethyl orthobutyrate and triethyl orthobutyrate) and orthobenzoicacid alkyl esters (such as trimethyl orthobenzoate and triethyl orthobenzoate), among which orthoformicacid alkyl esters are preferable, and trimethyl orthoformate and triethyl orthoformate are more preferable.

The amount of the orthoester is preferably from 1 to 10 g equivalents based on 1 g equivalent of the (Z)-hydroxymethylcyclopropane compound, and more preferably from 1.2 to 2 g equivalents, in view of prevention of generation of material residues or by-products, and reaction efficiency.

The brønsted acid is not particularly limited and easily available ones can be used. Examples thereof include methanesulfonic acid, toluenesulfonic acid, trifluoromethanesulfonic acid, sulfuric acid and hydrogen chloride, among which methanesulfonic acid is preferable in view of reactivity.

The amount of the brønsted acid is preferably from 1 to 10 g equivalents based on 1 g equivalent of the (Z)-hydroxymethylcyclopropane compound, and more preferably from 1 to 1.5 g equivalents, in view of completion of the reaction or reaction efficiency.

The first step can generally be conducted in a solvent, and an orthoester can also serve as the solvent. The solvent is not limited as long as it does not inhibit the reaction, and hydrocarbon solvents such as toluene and aprotic polar solvents such as N, N-dimethylformamide can be used alone or in combination. The amount of the solvent is preferably 5 parts by weight or less based on 1 part by weight of the (Z)-hydroxymethylcyclopropane compound.

The reaction temperature of the first step is generally from 0 to 100° C., and preferably from 20 to 40° C. The reaction time is generally from 1 to 24 hours, and preferably from 1 to 10 hours.

In the reaction mixture after completion of the first step, the iminium salt (I), its counter ion is conjugated base of the used brønsted acid, is contained. The reaction mixture, as it is, can be used for the second step. The first step and the second step can be conducted in the same reaction vessel, so called in one-pot. In such a case, before the second step, the reaction mixture after completion of the first step can be concentrated and substituted by another solvent.

Also, the iminium salt (I) can be isolated by removing the solvent under reduced pressure, and may be optionally purified by conventional means such as decantation with an organic solvent or chromatography.

The iminium salt (I) produced in the first step is a novel compound, and a useful synthetic intermediate of the (Z)-aminomethylcyclopropane compound hydrochloride as an antidepresent. A⁻ in the iminium salt (I) is preferably $CH_3SO_3^-$.

The second step can be conducted, for example, by mixing the reaction mixture after completion of the first step or the isolated iminium salt (I) with a phthalimidating agent in a solvent. Although an addition order is not particularly limited, a method of adding dropwise the reaction mixture after completion of the first step to the phthalimidating agent is preferable.

As the phthalimidating agent, a phthalimide salt is used. Examples thereof include phthalimide potassium salt, phthalimide sodium salt and phthalimide triethylamine salt, among which phthalimide potassium salt is preferred. The amount of the phthalimidating agent is preferably from 1 to 10 g equivalents based on 1 g equivalent of the (Z)-hydroxymethylcyclopropane compound (1 g equivalent of the iminium salt (I), assuming that the yield of the iminium salt (I) in the first step is 100%) that is used in the first step, and more preferably from 1 to 2 g equivalents, in view of completion of the reaction or reaction efficiency.

The phthalimide salt may be produced from phthalimide and a base in a reaction system. In this case, examples of the base include
at least one kind of potassium tert-butoxide, sodium methoxide, potassium carbonate, triethylamine and the like. The amount of the base is preferably from 1 to 10 g equivalents, and more preferably from 1 to 2 g equivalents, based on 1 g equivalent of phthalimide.

The second step is preferably conducted in a solvent. Examples of the solvent include single solvents and mixed solvents such as aprotic polar organic solvents (such as N,N-dimethylformamide, N,N-dimethylacetoamide, N,N'-dimethylimidazolidinone and N-methyl pyrrolidone) and protic organic solvents (such as methanol, ethanol, n-propanol, isopropanol, n-butanol, isobutanol, tert-butanol, ethylene glycol and propylene glycol), among which aprotic polar organic solvents are preferred in view of reactivity, and N,N-dimethylformamide and N,N-dimethylacetoamide are particularly preferred. The amount of the solvent is preferably from 1 to 50 parts by weight based on 1 part by weight of the (Z)-hydroxymethylcyclopropane compound that is used in the first step.

The reaction temperature of the second step is generally from 0 to 150° C., and preferably from 20 to 80° C. The reaction time is generally from 1 to 20 hours, and preferably from 1 to 5 hours.

After completion of the second step, the (Z)-phthalimidomethylcyclopropane compound can be isolated and purified by a conventional method. For example, isolation can be conducted by adding water or the like to the reaction mixture, filtering and washing the precipitated crystal, or extracting the reaction mixture with an organic solvent, followed by washing with water, and concentration. Furthermore, purification may be conducted by crystallization or chromatography.

The (Z)-aminomethylcyclopropane compound hydrochloride, which is useful as an antidepresent, can be derived from the (Z)-phthalimidomethylcyclopropane compound obtained by the present invention by a known method. For example, as described in Japanese Examined Patent Publication No. 5-67136, the (Z)-aminomethylcyclopropane compound hydrochloride can be derived by reacting the (Z)-phthalimidomethylcyclopropane compound with an aqueous methylamine solution to obtain the (Z)-aminomethylcyclopropane compound, and treating the compound with hydrogen chloride.

The (Z)-hydroxymethylcyclopropane compound is a known compound, and as described in JPH02-262558-A, for example, the compound can be produced by reacting 2-oxo-1-phenyl-3-oxabicyclo[3.1.0]hexane (see synthesis, 1978, 304-305) with diethylamine in the presence of a Lewis acid amine complex. However, since a low boiling point halogenated hydrocarbon such as dichloroethane is required in this method, there arises an environmental problem similarly to the above described conventional process for producing the (Z)-phthalimidomethylcyclopropane compound.

Accordingly, a method of reacting 2-oxo-1-phenyl-3-oxabicyclo[3.1.0]hexane with diethylamine in the presence of an alkali metal alkoxide, which is proposed by the present inventors, is preferable.

The method can be conducted, for example, by mixing 2-oxo-1-phenyl-3-oxabicyclo[3.1.0]hexane, diethylamine and an alkali metal alkoxide in a solvent.

The amount of diethylamine is generally from 1 to 10 g equivalents, and preferably from 2 to 4 g equivalents, based on 1 g equivalent of 2-oxo-1-phenyl-3-oxabicyclo[3.1.0]hexane.

Examples of the alkali metal alkoxide include alkali metal salts of an alcohol having 1 to 4 carbon atoms, such as lithium methoxide, sodium methoxide, potassium methoxide, lithium ethoxide, sodium ethoxide, potassium ethoxide, sodium t-butoxide and potassium t-butoxide. Sodium methoxide or potassium methoxide is preferred, and sodium methoxide is particularly preferred.

The amount of the alkali metal alkoxide is generally from 1 to 5 g equivalents, and preferably from 1.5 to 4 g equivalents, based on 1 g equivalent of 2-oxo-1-phenyl-3-oxabicyclo[3.1.0]hexane.

The form of the alkali metal alkoxide is not particularly limited, and it may be in the form of solid or solution. When a solution is used, a solution of the alcohol solvent corresponding to an alkali metal alkoxide to be used (for example, sodium methoxide in methanol) is preferably selected. The alcohol solvent is contained as a portion of a reaction solvent.

The kind of the solvent to be used is not limited as long as it does not inhibit the reaction, and examples thereof include methanol, ethanol, toluene, hexane, heptane and the like. These solvents can be used alone or in combination.

The amount of the solvent is generally from 1 to 10 ml, and preferably from 3 to 5 ml, based on 1 g of 2-oxo-1-phenyl-3-oxabicyclo[3.1.0]hexane.

The reaction temperature is generally from 0 to 100° C., preferably from 20 to 80° C., and particularly preferably from 20 to 30° C., and the reaction time is generally from 3 to 30 hours, although it varies depending on the reaction amount, the reaction temperature or the like.

After completion of the reaction, the (Z)-hydroxymethylcyclopropane compound can be obtained by any of known isolation or purification methods in the field or in combination thereof, such as extraction with a solvent, silica gel column chromatography, high performance liquid chromatography, distillation under reduced pressure and recrystallization.

Hereinafter, the present invention will be described in more detail by way of examples, but the present invention is not limited thereto.

Preparation Example 1

(Z)-1-phenyl-1-(N,N-diethylaminocarbonyl)-2-hydroxymethylcyclopropane

Diethylamine (250.4 g, 3.42 mol) was added to a mixture solution of 2-oxo-1-phenyl-3-oxabicyclo[3.1.0]hexane (198.8 g, 1.14 mol) and toluene (198.8 g), and a 28% sodium methoxide/methanol solution (660.4 g, 3.42 mol) was added dropwise at 20 to 30° C., followed by stirring for 8 hours. The reaction solution after stirring was added dropwise to a mixture solution of water (554.8 g) and toluene (596.4 ml), and then acetic acid (226.0 g) was added dropwise, followed by separation of the solution. The obtained aqueous layer was extracted again with toluene (397.6 ml). The organic layers were combined, washed with water, and concentrated under reduced pressure to obtain the title compound as a 50% toluene solution. (It was confirmed by HPLC analysis (HPLC: LC-10Avp, ODS column 4.6 mm×150 mm, manufactured by Shimadzu Co.) that the title compound was contained in an amount of 265.3 g. The yield was 93.8%.)

Example 1

(Z)-1-phenyl-1-(N,N-diethylaminocarbonyl)-2-phthalimidomethylcyclopropane

Ethyl orthoformate (14.4 g, 0.097 mol) was added to a toluene solution (40.0 g) containing (Z)-1-phenyl-1-(N,N-diethylaminocarbonyl)-2-hydroxymethylcyclopropane (20.0 g, 0.081 mol) in a reaction vessel, and then methanesulfonic acid (9.5 g, 0.089 mol) was added dropwise at 15 to 35° C. over one hour. After the instillation, the solution was stirred for 1.5 hours, heated to 40° C., and concentrated under reduced pressure. N,N-dimethylformamide (20 ml) was added, followed by concentration under the same conditions to obtain a concentrated solution (47.1 g).

Separately, phthalimide potassium salt (18.7 g, 0.101 mol) and 92 ml of N,N-dimethylformamide were charged in a reaction vessel, and the afore-mentioned concentrated solution was added dropwise to the obtained solution at 40° C. over 2 hours, followed by stirring for one hour.

The reaction solution was cooled to about 20° C., and water (67.5 ml) was added dropwise to the cooled reaction solution over 3 hours. The mixture was filtered, washed with water (67.5 ml), and dried at about 60° C. under reduced pressure to obtain the title compound (28.8 g) as a white crystal. The yield was 93.2% and the purity was 98.6%.
Physical data: $^1$H-NMR (CD$_3$OD, 400 MHz) δ: 0.62 (3H, t, J=7.0 Hz), 1.11 (1H, dd, J=5.2, 8.8 Hz), 1.17 (3H, t, J=7.0 Hz), 1.63 (1H, dd, J=5.2, 6.0 Hz), 2.25 (1H, m), 3.18 (1H, m), 3.30-3.43 (3H, m), 3.67 (1H, m), 4.07 (1H, dd, J=5.0, 14.2 Hz), 7.21-7.34 (5H, m), 7.80-7.89 (4H, m).

Example 2

(Z)-1-phenyl-1-(N,N-diethylaminocarbonyl)-2-aminomethylcyclopropane hydrochloride Water (35.0 kg) and toluene (79.0 kg) were added to (Z)-1-phenyl-1-(N,N-diethylaminocarbonyl)-2-phthalimidomethylcyclopropane (18.2 kg, 48.4 mol), and a 40 wt % aqueous solution of monomethylamine (37.7 kg, 485 mol) was added dropwise to the mixture, followed by stirring at 20° C. for 20 hours. After separation of the reaction mixture, the aqueous layer was extracted twice with toluene. The organic layers were combined, dried over magnesium sulfate, filtered and then concentrated under reduced pressure. Ethyl acetate (67.1 kg) and isopropyl alcohol (9.0 kg) were added to the concentrated residue, and 4N hydrogen chloride-ethyl acetate (12.5 kg, 55.9 mol) was added dropwise to a solution thereof. The resulting crystal was filtered, washed with ethyl acetate and dried to obtain (Z)-1-phenyl-1-(N,N-diethylaminocarbonyl)-2-aminomethylcyclopropane hydrochloride (11.9 kg) as a white powder. The yield was 86.9%.

Physical data: $^1$H-NMR (D$_2$O, 400 MHz) δ: 0.87 (3H, t, J=7.0 Hz), 1.08 (3H, t, J=7.0 Hz), 1.72-1.84 (3H, m), 2.43 (1H, m), 3.25-3.44 (4H, m), 3.71 (1H, m), 7.13-7.28 (5H, m), 8.80 (3H, br-s).

Example 3

N,N-diethyl-(1-phenyl-3-oxabicyclo[3.1.0]hex-2-ylidene)iminium methanesulfonate

A concentrated solution before conducting phthalimidation was produced in the same manner as in Example 1, and some of the concentrated solution was taken and evaporated to dryness under reduced pressure. After adding n-heptane to the residue, a decantation operation was repeated several times, followed by evaporation to dryness under reduced pressure to obtain the title compound as a water-soluble pale yellow oil (purity: 98.6%).

Physical data: $^1$H-NMR (D$_2$O, 400 MHz) δ: 0.26 (3H, t, J=7.2 Hz), 0.71 (3H, t, J=7.2 Hz), 1.14 (1H, m), 1.90 (1H, m), 2.18 (1H, m), 2.24 (3H, s), 2.75 (1H, m), 2.95 (1H, m), 3.13 (2H, m), 4.30 (1H, d, J=9.6 Hz), 4.57 (1H, dd, J=4.8, 9.6 Hz), 6.93-7.00 (5H, m). LC-MS (ESI, transfer phase: acetonitrile 0.1% aq. CF$_3$CO$_2$H) M$^{+1}$: 344 (detected by trifluoroaceticacid salt)

CI-MS: M$^{+1}$ 326

According to the present invention, in the case of producing the (Z)-phthalimidomethylcyclopropane compound, a chlorination agent, which generates sulfur dioxide during the reaction, is not required because a chloro compound or an acid chloride is not by way of the reaction, unlike a conventional method. Furthermore, it is not required to use a low boiling point halogenated hydrocarbon solvent such as dichloroethane, which may cause an environmental problem.

Also, as compared to the case where a chlorination agent is used, coloration of the product can be suppressed and thus the process of the present invention is excellent as a process for producing an intermediate of drugs.

Furthermore, since a first step and a second step are conducted in the same reaction vessel, one step can substantially be omitted, and thus the process of the present invention is also excellent in economy.

The invention claimed is:

1. A process for producing (Z)-1-phenyl-1-(N,N-diethylaminocarbonyl)-2-phthalimidomethylcyclopropane, comprising:
   reacting (Z)-1-phenyl-1-(N,N-diethylaminocarbonyl)-2-hydroxymethylcyclopropane with an orthoester and a brønsted acid to obtain a reaction product, and then reacting the reaction product with a phthalimidating agent wherein the reaction product of (Z)-1-phenyl-1-(N,N-diethylaminocarbonyl)-2-hydroxymethylcyclopropane, an orthoester and a brønsted acid is an iminium salt of the formula (I)

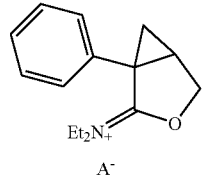

(I)

wherein A$^-$ represents conjugated base of brønsted acid.

2. The process according to claim 1, wherein the brønsted acid is methanesulfonic acid.

3. The process according to claim 1, wherein the orthoester is an orthoformic alkyl ester.

4. The process according to claim 3, wherein the orthoformic alkyl ester is triethyl orthoformate or trimethyl orthoformate.

5. The process according to claim 1, wherein the phthalimidating agent is (1) phthalimide potassium salt or (2) phthalimide and a base.

6. The process according to claim 5, wherein the base is at least one selected from the group consisting of potassium tert-butoxide, sodium methoxide, potassium carbonate and triethylamine.

7. The process according to claim 1, wherein (Z)-1-phenyl-1-(N,N-diethylaminocarbonyl)-2-hydroxymethylcyclopropane is the compound obtained by reacting 2-oxo-1-phenyl-3-oxabicyclo[3.1.0]hexane with diethylamine in the presence of an alkali metal alkoxide.

8. A process for producing (Z)-1-phenyl-1-(N,N-diethylaminocarbonyl)-2-aminomethylcyclopropane hydrochloride, comprising:
   reacting (Z)-1-phenyl-1-(N,N-diethylaminocarbonyl)-2-hydroxymethylcyclopropane with an orthoester and a brønsted acid to obtain a reaction product,
   reacting the reaction product with a phthalimidating agent to obtain (Z)-1-phenyl-1-(N,N-diethylaminocarbonyl)-2-phthalimidomethylcyclopropane,
   reacting (Z)-1-phenyl-1-(N,N-diethylaminocarbonyl)-2-phthalimidomethylcyclopropane with aqueous methylamine to obtain (Z)-1-phenyl-1-(N,N-diethylaminocarbonyl)-2-aminomethylcyclopropane, and
   treating (Z)-1-phenyl-1-(N,N-diethylaminocarbonyl)-2-aminomethylcyclopropane with hydrogen chloride,
   wherein the reaction product of (Z)-1-phenyl-1-(N,N-diethylaminocarbonyl)-2-hydroxymethylcyclopropane, an orthoester and a brønsted acid is an iminium salt of the formula (I)

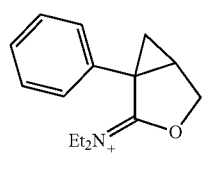

(I)

wherein A$^-$ represents conjugated base of brønsted acid.

* * * * *